(12) United States Patent
Zhou et al.

(10) Patent No.: US 10,493,195 B2
(45) Date of Patent: Dec. 3, 2019

(54) INTEGRATED ON-LINE MONITORING AND THERMOSTATIC HEATING APPARATUS FOR BIOARTIFICIAL LIVER DEVICE

(71) Applicant: WUHAN TOGO MEDITECH CO., LTD, Wuhan (CN)

(72) Inventors: Ping Zhou, Wuhan (CN); Lu Liu, Wuhan (CN)

(73) Assignee: WUHAN TOGO MEDITECH CO., LTD, Wuhan (CN)

( * ) Notice: Subject to any disclaimer, the term of this patent is extended or adjusted under 35 U.S.C. 154(b) by 171 days.

(21) Appl. No.: 15/853,836

(22) Filed: Dec. 24, 2017

(65) Prior Publication Data

US 2018/0117235 A1 May 3, 2018

Related U.S. Application Data

(63) Continuation-in-part of application No. PCT/CN2016/106022, filed on Nov. 16, 2016.

(30) Foreign Application Priority Data

Jul. 29, 2016 (CN) .......................... 2016 1 0609169

(51) Int. Cl.
*A61M 1/34* (2006.01)
*C12M 3/00* (2006.01)
(Continued)

(52) U.S. Cl.
CPC ........ *A61M 1/3489* (2014.02); *A61M 1/1664* (2014.02); *C12M 3/00* (2013.01);
(Continued)

(58) Field of Classification Search
CPC .............. A61M 1/3489; A61M 1/1664; A61M 1/1698; A61M 1/1662; A61M 1/1629;
(Continued)

(56) References Cited

U.S. PATENT DOCUMENTS 6,372,482 B1 * 4/2002 Mitrani ............... A61M 1/3472
210/601

FOREIGN PATENT DOCUMENTS

CN 1231212 * 4/1998 ............ C12M 29/04
CN 101549179 * 4/2009 .......... A61M 1/1625
(Continued)

OTHER PUBLICATIONS

ISR for PCT/CN2016/106022 A1 (English language version) (Year: 2017).*

*Primary Examiner* — Michael L Hobbs
(74) *Attorney, Agent, or Firm* — Matthias Scholl P.C.; Matthias Scholl (57) ABSTRACT

An integrated on-line monitoring and thermostatic heating apparatus for a bioartificial liver device, the apparatus including a blood inlet, a blood pump, an arterial drip chamber, a bioreactor module, a venous drip chamber, and a blood reinfusion port which are connected in sequence. The bioreactor module includes a thermostatic water tank and a bioreactor disposed in the thermostatic water tank. The bioreactor includes a container, and a first partition and a second partition which are disposed in the container. The first partition and the second partition separate the container into three independent parts, that is, a plasma separator, an oxygenator, and a reactor. The plasma separator and the oxygenator are connected through an external connection pipe. The external connection pipe is equipped with a separation pump. The second partition includes a communication hole, and the reactor and the oxygenator are connected through the communication hole.

12 Claims, 4 Drawing Sheets

(51) Int. Cl.
*A61M 1/16* (2006.01)
*C12M 1/00* (2006.01)
*A61F 2/00* (2006.01)

(52) U.S. Cl.
CPC ............ *C12M 21/08* (2013.01); *C12M 23/34* (2013.01); *C12M 29/04* (2013.01); *C12M 29/10* (2013.01); *A61F 2/00* (2013.01); *A61M 1/1629* (2014.02); *A61M 1/1662* (2014.02); *A61M 1/1698* (2013.01); *A61M 2202/0413* (2013.01); *A61M 2205/3368* (2013.01); *A61M 2205/36* (2013.01); *A61M 2210/1071* (2013.01)

(58) Field of Classification Search
CPC ...... A61M 2210/1071; A61M 2205/36; A61M 2202/0413; A61F 2/00
See application file for complete search history.

(56) References Cited

FOREIGN PATENT DOCUMENTS

| | | | | |
|---|---|---|---|---|
| CN | 102225222 | * | 2/2011 | .......... A61M 1/3489 |
| CN | 205356253 | * | 12/2015 | ................ A61J 1/05 |

* cited by examiner

FIG. 4

INTEGRATED ON-LINE MONITORING AND THERMOSTATIC HEATING APPARATUS FOR BIOARTIFICIAL LIVER DEVICE

CROSS-REFERENCE TO RELATED APPLICATIONS

This application is a continuation-in-part of International Patent Application No. PCT/CN2016/106022 with an international filing date of Nov. 16, 2016, designating the United States, now pending, and further claims foreign priority benefits to Chinese Patent Application No. 201610609169.6 filed Jul. 29, 2016. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND OF THE INVENTION

Field of the Invention

The present disclosure relates to an integrated on-line monitoring and thermostatic heating apparatus for a bioartificial liver device.

Description of the Related Art

Bioartificial liver support systems use cell population with liver metabolic function to purify the blood from patients suffering from liver diseases, achieving the function of liver support in vitro. The oxygen content, temperature and pH environment in the support systems are closely related to the bioactivity of the cell population.

Existing bioartificial liver devices only use a heater to maintain the ambient temperature of the cell population. The heating is unstable, which has a negative impact on the work efficiency of the bioartificial liver device. And the pH value in the bioartificial liver device is nonadjustable.

In addition, typical bioartificial liver devices are of a hollow fiber type, in which the fiber tubes are closely arranged, and the space between every two adjacent fiber tubes is narrow. As a result, it is difficult for the liver cells to enter the central space of the fiber tubes, leading to nonuniform cell distribution and decreased detoxification performance.

SUMMARY OF THE INVENTION

It is an objective of the present disclosure to provide an integrated on-line monitoring and thermostatic heating apparatus for a bioartificial liver device. In this apparatus, four parts, i.e., a plasma separator, an oxygenator, a heater, and a bioreactor are combined to form a four-in-one device, so that the functions of pH regulation, stable heating at a constant temperature, uniform cell distribution, and full substance exchange are all achieved, increasing the growth density and bioactivity of liver cells.

To achieve the above objective, in accordance with one embodiment of the invention, there is provided an integrated on-line monitoring and thermostatic heating apparatus for a bioartificial liver device, the apparatus comprising a blood inlet, a blood pump, an arterial drip chamber, a bioreactor module, a venous drip chamber, and a blood reinfusion port which are connected in sequence.

The bioreactor module comprises a thermostatic water tank and a bioreactor disposed in the thermostatic water tank.

The bioreactor comprises a container, and a first partition and a second partition which are disposed in the container. The first partition and the second partition separate the container into three independent parts, that is, a plasma separator, an oxygenator, and a reactor.

Inner cavities of the plasma separator and the oxygenator are connected through an external connection pipe. The external connection pipe is equipped with a separation pump. The second partition comprises a communication hole, and inner cavities of the reactor and the oxygenator are connected through the communication hole.

The container comprises a blood/pre-filled liquid inlet at an upper end thereof and a blood cell outlet at a lower end thereof. The plasma separator comprises hollow fiber bundles. The blood/pre-filled liquid inlet communicates with the blood cell outlet through the hollow fiber bundles in the plasma separator.

The container also comprises an oxygen/carbon dioxide inlet at the upper end thereof, the oxygenator comprises breathable fiber membrane tubes, and the oxygen/carbon dioxide inlet communicates with the breathable fiber membrane tubes in the oxygenator.

The container further comprises a nutrient liquid/liver cell suspension inlet, a nutrient liquid/liver cell suspension outlet, and a plasma/pre-filled liquid outlet. The reactor comprises a plurality of hollow fiber membrane tubes and a plurality of wool yarns. The communication hole communicates with the plasma/pre-filled liquid outlet through the plurality of hollow fiber membrane tubes disposed in the reactor. The plurality of wool yarns is parallel to, spaced from, and alternates with the plurality of the hollow fiber membrane tubes.

The thermostatic water tank comprises a shell, and a hot water inlet and a hot water outlet disposed on the shell. The shell encloses the bioreactor. The shell comprises a plurality of bores corresponding to inlets and outlets of the bioreactor. The inlets and outlets of the bioreactor are filled with nozzles comprising an outer wall, and the outer wall of the nozzles is in sealed connection with walls enclosing the bores.

The blood/pre-filled liquid inlet is connected to an outlet of the arterial drip chamber, and the plasma/pre-filled liquid outlet and the blood cell outlet are both connected to an inlet of the venous drip chamber.

In a class of this embodiment, the external connection pipe comprises a liquid inlet end connected to a lower end of the plasma separator, and a liquid outlet end connected to a lower end of the oxygenator; and the communication hole is located at an upper end of the second partition.

In a class of this embodiment, the oxygenator further comprises a horizontally disposed a sealed stent plate for blocking the penetration of the plasma/pre-filled liquid. The sealed stent plate is located above the communication hole and comprises a plurality of orifices. An upper end of the breathable fiber membrane tubes is clamped in the orifices. A space exists between the sealed stent plate and a top wall of the oxygenator, and the breathable fiber membrane tubes communicate with the oxygen/carbon dioxide inlet through the space formed by the sealed stent plate and the top wall of the oxygenator.

The further solution described above has the following beneficial effects. By fixing the breathable fiber membrane tubes in the oxygenator through the sealed stent plate, it can be ensured that the oxygen/carbon dioxide inlet is in communication with the breathable fiber membrane tubes so as to allow passage of gas while blocking the plasma/pre-filled liquid.

In a class of this embodiment, two polyurethane resin stent plates are horizontally disposed at an upper end and a lower end of the plasma separator respectively for blocking the penetration of cells and liquid. The two polyurethane resin stent plates are spaced from a top end and a bottom end of the plasma separator. The two polyurethane resin stent plates comprise a plurality of through holes, two ends of the hollow fiber bundle are clamped in the through holes of the two polyurethane resin stent plates, respectively; and the liquid inlet end of the external connection pipe is located between the two polyurethane resin stent plates. Instead of inserting all the ends of the hollow fiber bundles into the blood/prefilled inlet and the blood cell outlet, the provision of the polyurethane resin stent plates allows the hollow fiber bundles to be distributed uniformly inside the plasma separator.

In a class of this embodiment, two polyurethane resin stent plates are horizontally disposed at an upper end and a lower end of the reactor respectively for blocking the penetration of cells and liquid. The two polyurethane resin stent plates are spaced from a top end and a bottom end of the reactor. The two polyurethane resin stent plates comprise a plurality of through holes, two ends of the hollow fiber membrane tubes are clamped in the through holes of the two polyurethane resin stent plates, respectively; the communication hole is located above the polyurethane resin stent sheets. The nutrient liquid/liver cell suspension inlet and outlet are located between the two polyurethane resin stent sheets. Provision of the polyurethane resin stent sheets enables the hollow fiber membrane tubes to be distributed uniformly inside the reactor.

In a class of this embodiment, the plasma separator further comprises an auxiliary inlet and an auxiliary outlet disposed between the two polyurethane resin stent plates; the oxygenator comprises an auxiliary outlet at a lower end thereof; the liquid inlet end of the external connection pipe communicates with the auxiliary outlet of the plasma separator; the liquid outlet end of the external connection pipe communicates with the auxiliary outlet of the oxygenator.

In a class of this embodiment, the wool yarns comprise a plurality of uniformly distributed wools woven from velvets and the wools on the wool yarns are short wools.

In a class of this embodiment, the apparatus further comprises a biochemical monitoring device for continuous on-line monitoring of biochemical indexes. The biochemical monitoring device comprises a monitoring and controlling apparatus, a signal feedback apparatus, and an upstream biochemical index probe and a downstream biochemical index probe connected to the monitoring and controlling apparatus through electrical signals. The upstream biochemical index probe is disposed close to the blood inlet, and the downstream biochemical index probe is disposed close to the blood reinfusion port.

In a class of this embodiment, branch pipes for adding drug or liquid are provided respectively on the arterial drip chamber, on the venous drip chamber, and between the blood pump and the blood inlet. A heparin branch pipe for injecting heparin is provided between the blood pump and the arterial drip chamber. An air monitoring device for monitoring air in the pipeline is provided between the venous drip chamber and the blood reinfusion port. A heating apparatus for heating the hot water entering the thermostatic water tank and a temperature regulation apparatus for regulating the water temperature are provided between the arterial drip chamber and the bioreactor module.

In a class of this embodiment, the apparatus also comprises a plurality of pressure detection devices disposed respectively on the arterial drip chamber, on the venous drip chamber, and between the blood inlet and the blood pump.

Advantages of the integrated on-line monitoring and thermostatic heating apparatus for a bioartificial liver device according to embodiments of the present disclosure are summarized as follows:

1. By combining the four parts, i.e., the plasma separator, the oxygenator, the heater, and the bioreactor to constitute the on-line monitoring and thermostatic heating apparatus, the resulting bioartificial liver support system has a simpler structure and is easy to operate.

2. Once blood enters the plasma separator, the plasma separated by the hollow fiber bundles enters the oxygenator and the reactor sequentially, thereby saving unnecessary pipelines.

3. By providing a breathable fiber membrane inside the oxygenator in a zigzag manner to supply a sufficient amount of oxygen to the reactor while adjusting the pH by introducing an appropriate amount of carbon dioxide into the breathable fiber membrane at a suitable time, an environment with a more stable pH can be maintained in the bioreactor, thereby providing an appropriate metabolic environment for cells and guarantying the cell activity.

4. The thermostatic water tank encloses the bioreactor, so that the liver cells in the bioreactor can be heated in a water bath at a constant temperature, thereby achieving uniform and stable heating, and saving the space.

5. A plurality of wools is uniformly distributed on the wool yarns, thereby increasing the adherent area of the liver cells as well as promoting adherent growth of the liver cells.

6. The wool yarns provide a stent for liver cells perfused into the inner container of the reactor, ensuring suitable conditions in the container of the reactor for adherent growth of the liver cells, while reducing the adherence of the liver cells to the hollow fiber membrane tubes and preventing cells from clogging micropores in the membrane wall of the hollow fiber membrane tubes, thereby facilitating normal substance exchange between inside and outside the hollow fiber membrane tubes.

7. The wool yarns and the hollow fiber membrane tubes are arranged to be parallel and alternate at intervals, or in a honeycomb shape, or in a one-surrounded-by-three pattern, ensuring the uniform distribution of the liver cells in the inner container of the reactor and improving the activity and utilization of the liver cells.

8. The biochemical monitoring device enables the apparatus to on-line monitor biochemical indexes, plasma, or blood pressure in real time.

9. By increasing the adherent area of liver cells in the reactor and improving the uniformity of liver cell distribution, desirable cell activity can be maintained, thereby maximizing the liver cell function and achieving the optimum therapeutic effect.

In the drawings, the following reference numbers are used: 1 bioreactor, 1.1 plasma separator, 1.1.1 blood/pre-filled liquid inlet, 1.1.2 blood cell outlet, 1.1.3 backup sample inlet of the plasma separator, 1.1.4 sample outlet of the plasma separator, 1.2 oxygenator, 1.2.1 oxygen/carbon dioxide inlet, 1.2.2 infusion sample inlet, 1.2.3 backup sample inlet of the oxygenator, 1.2.4 sample outlet of the oxygenator, 1.3 reactor, 1.3.1 nutrient liquid/liver cell suspension inlet, 1.3.2 nutrient liquid/liver cell suspension outlet, 1.3.3 plasma/pre-filled liquid outlet, 1.4 container, 1.5 first partition, 1.6 second partition, 2 thermostatic water tank, 2.1 shell, 2.1.1 bore, 2.2 hot water inlet, 2.3 hot water outlet, 3 blood pump, 4 arterial drip chamber, 5 bioreactor module, 6 venous drip chamber, 7 blood reinfusion port, 8 hollow fiber bundle, 9 breathable fiber membrane tubes, 10 hollow fiber membrane tube, 11 wool, 12 communication hole, 13 biochemical monitoring device, 13.1 monitoring and controlling apparatus, 13.2 signal feedback apparatus, 13.3 upstream biochemical index probe, 13.4 downstream biochemical index probe, 14 polyurethane resin stent plate, 15 polyurethane resin stent sheet, 16 polyethersulfone filtration membrane, 17 branch pipe, 18 heparin branch pipe, 19 air monitoring device, 20 pressure detection device, 21 sealed stent plate, 22 heating apparatus, 23 temperature regulation apparatus, 24 blood inlet, 25 separation pump, 26 backup micro-pump port, 27 external connection pipe, 28 wool yarn.

DETAILED DESCRIPTION OF THE EMBODIMENTS

The present disclosure will be further described below in detail with reference to the accompanying drawings and specific embodiments.

An integrated on-line monitoring and thermostatic heating apparatus for a bioartificial liver device shown in FIGS. 1, 2, 3, and 4 comprises a blood inlet 24, a blood pump 3, an arterial drip chamber 4, a bioreactor module 5, a venous drip chamber 6, and a blood reinfusion port 7 connected in sequence.

The bioreactor module 5 comprises a thermostatic water tank 2 and a bioreactor 1 disposed in the thermostatic water tank.

The bioreactor 1 comprises a container 1.4, and a first partition 1.5 and a second partition 1.6 disposed in the container 1.4. The first partition 1.5 and the second partition 1.6 separate the container 1.4 into three independent parts, i.e., a plasma separator 1.1, an oxygenator 1.2, and a reactor 1.3 in the order from left to right.

The plasma separator 1.1 and the oxygenator 1.2 are connected through an external connection pipe 27. The external connection pipe 27 is equipped with a separation pump 25. The reactor 1.3 and the oxygenator 1.2 are connected through a communication hole 12 provided in the second partition 1.6.

The left portion of the container 1.4 comprises a blood/pre-filled liquid inlet 1.1.1 at the upper end and a blood cell outlet 1.1.2 at the lower end. The blood/pre-filled liquid inlet 1.1.1 communicates with the blood cell outlet 1.1.2 through hollow fiber bundles 8 disposed inside the plasma separator 1.1.

The middle portion of the container 1.4 comprises an oxygen/carbon dioxide inlet 1.2.1 at the upper end, and breathable fiber membrane tubes 9 in communication with the oxygen/carbon dioxide inlet 1.2.1 are provided inside the oxygenator 1.2.

The right portion of the container 1.4 comprises a nutrient liquid/liver cell suspension inlet 1.3.1, a nutrient liquid/liver cell suspension outlet 1.3.2, and a plasma/pre-filled liquid outlet 1.3.3. The communication hole 12 communicates with the plasma/pre-filled liquid outlet 1.3.3 through the hollow fiber membrane tubes 10 in the reactor 1.3. A plurality of wool yarns 28 is provided inside the reactor 1.3 and is parallel to, spaced apart from, and alternates with the plurality of hollow fiber membrane tubes 10.

The thermostatic water tank 2 comprises a shell 2.1 and a hot water inlet 2.2 and a hot water outlet 2.3 provided on the shell 2.1. The shell 2.1 encloses the bioreactor 1. A plurality of bores 2.1.1 for passage of each inlet and outlet of the bioreactor 1 is also provided on the shell 2.1. Each inlet and outlet of the bioreactor 1 is a pipe opening with its outer wall in sealed connection with an inner wall of the bore 2.1.1.

The blood/pre-filled liquid inlet 1.1.1 is connected to the outlet of the arterial drip chamber 4, and the plasma/pre-filled liquid outlet 1.3.3 and the blood cell outlet 1.1.1 are both connected to the inlet of the venous drip chamber 6.

The liquid inlet end of the external connection pipe 27 is located at the lower end of the side wall of the plasma separator 1.1, and the liquid outlet end thereof is located at the lower end of the oxygenator 1.2. The communication hole 12 is located at the upper end of the second partition 1.6.

A sealed stent plate 21 is further provided inside the oxygenator 1.2 in the cross-sectional direction thereof for blocking the plasma/pre-filled liquid. The sealed stent plate 21 is located above the communication hole 12. A plurality of orifices is provided on the sealed stent plate 21. Each of the breathable fiber membrane tubes 9 has its upper end clamped in the orifice and is communicated with the oxygen/carbon dioxide inlet 1.2.1 through the space formed by the sealed stent plate 21 and the top of the inner container of the oxygenator 1.2. By fixing the breathable fiber membrane tubes in the oxygenator through the sealed stent plate, it can be ensured that the oxygen/carbon dioxide inlet is in communication with the breathable fiber membrane tubes to allow passage of gas while blocking the plasma/pre-filled liquid.

Two polyurethane resin stent plates 14 are further provided inside the plasma separator 1.1 in the cross-sectional direction thereof for blocking the passage of cells and liquid. The two polyurethane resin stent plates 14 are respectively located at the upper and lower ends of the plasma separator 1.1 and separated from the inner container at the ends of the plasma separator 1.1 by a distance. A plurality of through holes is provided on the polyurethane resin stent plates 14. Two ends of each hollow fiber bundle 8 are respectively clamped in the through holes of different polyurethane resin stent plates 14. The liquid inlet end of the external connection pipe 27 is located between the two polyurethane resin stent plates 14. Instead of inserting all the ends of the hollow fiber bundles into the blood/prefilled inlet and the blood cell outlet, provision of the polyurethane resin stent plates allows the hollow fiber bundles to be distributed uniformly inside the plasma separator.

Two polyurethane resin stent sheets 15 are further provided inside the reactor 1.3 in the cross-sectional direction thereof for blocking the passage of cells and liquid. The two polyurethane resin stent sheets 15 are respectively located at the upper and lower ends of the reactor 1.3 and are separated from the inner container at the ends of the reactor 1.3 by a distance. A plurality of through holes is provided on the polyurethane resin stent sheets 15. Two ends of the hollow fiber membrane tube 10 are respectively clamped in the through holes of different polyurethane resin stent sheets 15. The communication hole 12 is located above the polyurethane resin stent sheets 15. Nutrient liquid/liver cell suspension inlet 1.3.1 and outlet 1.3.2 are located between the two polyurethane resin stent sheets 15. Provision of the polyurethane resin stent sheets allows the hollow fiber membrane tubes to be distributed uniformly inside the reactor.

The left portion of the container 1.4 where the plasma separator 1.1 is located is further provided with a backup sample inlet 1.1.3 of the plasma separator and a sample outlet 1.1.4 of the plasma separator in communication with the inner container of the plasma separator 1.1 that are positioned between the two polyurethane resin stent plates 14. The lower end of the oxygenator 1.2 is provided with a sample outlet 1.2.4 of the oxygenator. A liquid inlet end of the external connection pipe 27 is in communication with the sample outlet 1.1.4 of the plasma separator. A liquid outlet end of the external connection pipe 27 and the sample outlet 1.2.4 of the oxygenator are in communication with the polyurethane resin stent plates 14.

The sample outlet 1.2.4 for the oxygenator is also provided with a backup micro-pump port 26 in communication therewith for supplying nutrients such as glucose.

Figure 4:
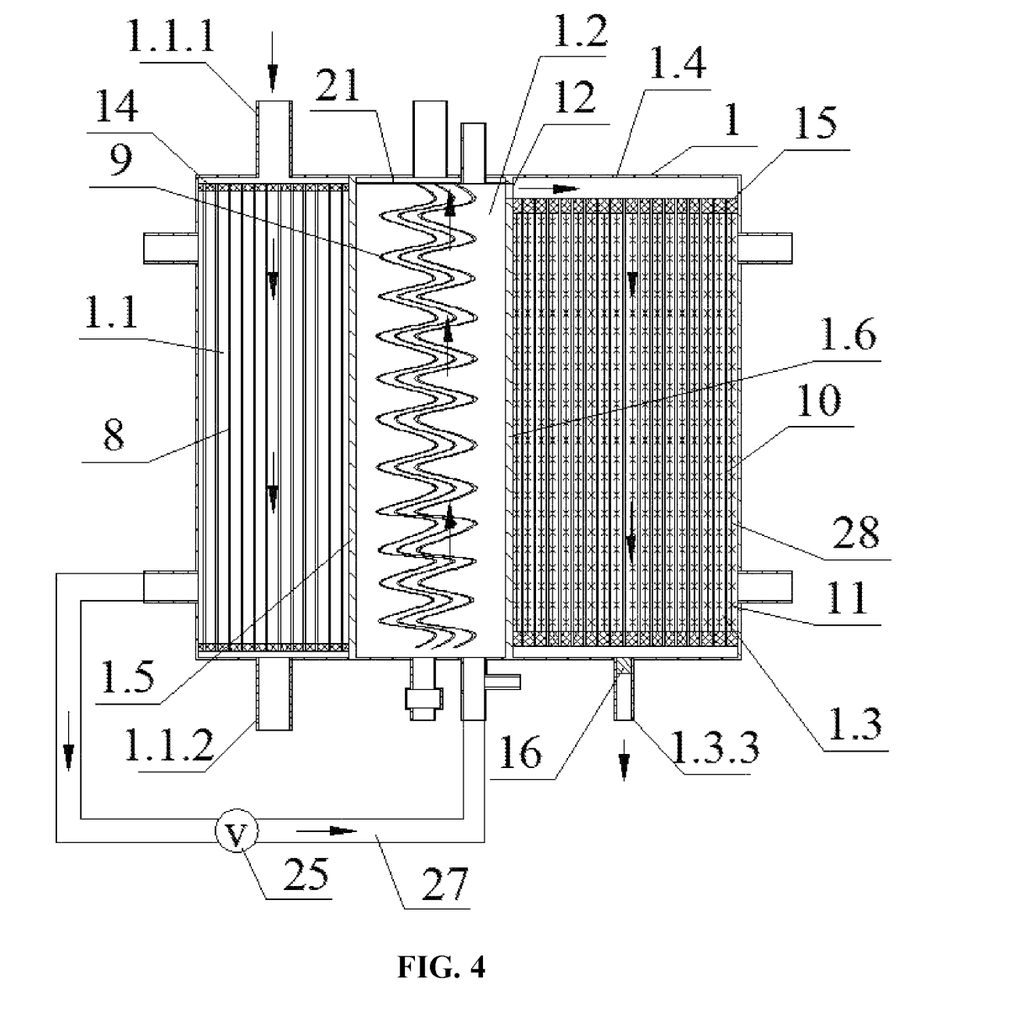
FIG. 4 is a cross-sectional view of a bioreactor in FIG. 3.

A plurality of wools 11 woven from velvets are distributed uniformly on the wool yarns 28 and the wools 11 on the wool yarns 28 are short wools.

Every three hollow fiber membrane tubes 10 surround one wool yarn 28, and every three wool yarns 28 surround one hollow fiber membrane tube 10. Alternatively, a plurality of the wool yarns 28 and a plurality of the hollow fiber membrane tubes 10 are arranged in a honeycomb shape. The hollow fiber membrane tubes 10 and the wool yarns 28 are arranged uniformly to be spaced equidistantly. The spacing between adjacent hollow fiber membrane tube 10 and wool yarn 28 is 50 to 200 µm.

The presence of the wool yarns 28 provides a stent for the adherence of liver cells to the inner container of the reactor 1.3 so as to facilitate uniform cell distribution, and the presence of the wools 11 increases the effective adherence area of the liver cells so as to maximize the effect of the liver cells.

The wool yarn 28 is a polyester fiber prepared by subjecting pure terephthalic acid or dimethyl terephthalate and ethylene glycol as raw materials to esterification or transesterification and polycondensation reaction to produce polyethylene terephthalate, which is then spun and biologically modified with fibronectin.

Figure 1:
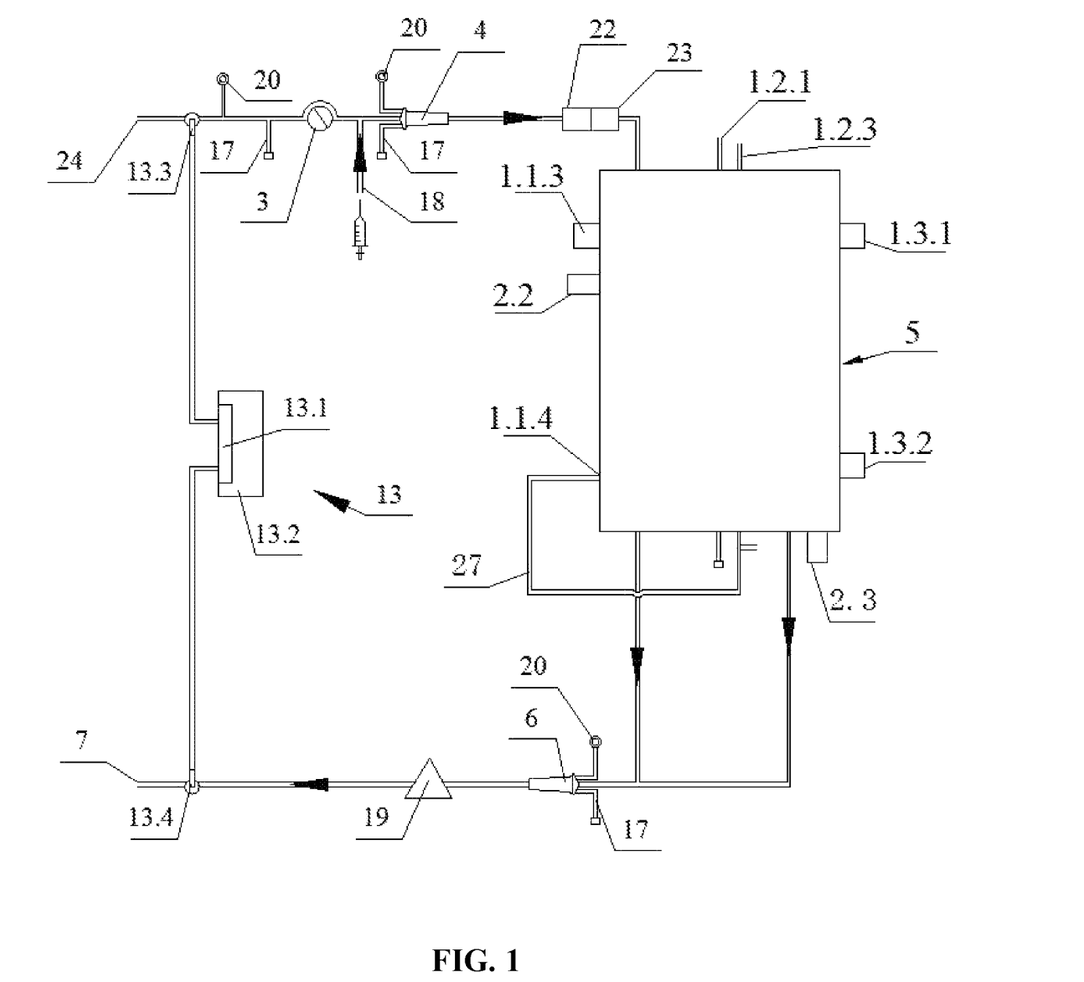
FIG. 1 is a schematic diagram of an integrated on-line monitoring and thermostatic heating apparatus for a bioartificial liver device according to the present disclosure.

The apparatus further comprises a biochemical monitoring device 13 for continuous on-line monitoring of biochemical indexes. The biochemical monitoring device 13 comprises a monitoring and controlling apparatus 13.1, a signal feedback apparatus 13.2, and an upstream biochemical index probe 13.3 and a downstream biochemical index probe 13.4 connected to the monitoring and controlling apparatus 13.1 through electrical signals. The upstream biochemical index probe 13.3 is disposed at the blood inlet 24, and the downstream biochemical index probe 13.4 is disposed close to the blood reinfusion port 7.

Branch pipes 17 for adding drug or liquid are provided respectively on the arterial drip chamber 4, on the venous drip chamber 6, and between the blood pump 3 and the blood inlet 24. A heparin branch pipe 18 for injecting heparin is provided between the blood pump 3 and the arterial drip chamber 4. An air monitoring device 19 is further disposed between the venous drip chamber 6 and the blood reinfusion port 7 for monitoring for the presence of gas in the pipeline.

A heating apparatus 22 for heating the hot water that enters the thermostatic water tank 2 and a temperature regulation apparatus 23 for regulating the water temperature are further provided between the arterial drip chamber 4 and the bioreactor module 5.

The apparatus further comprises a plurality of pressure detection devices 20 disposed respectively on the arterial drip chamber 4, on the venous drip chamber 6, and between the blood inlet 24 and the blood pump 3.

Figure 2:
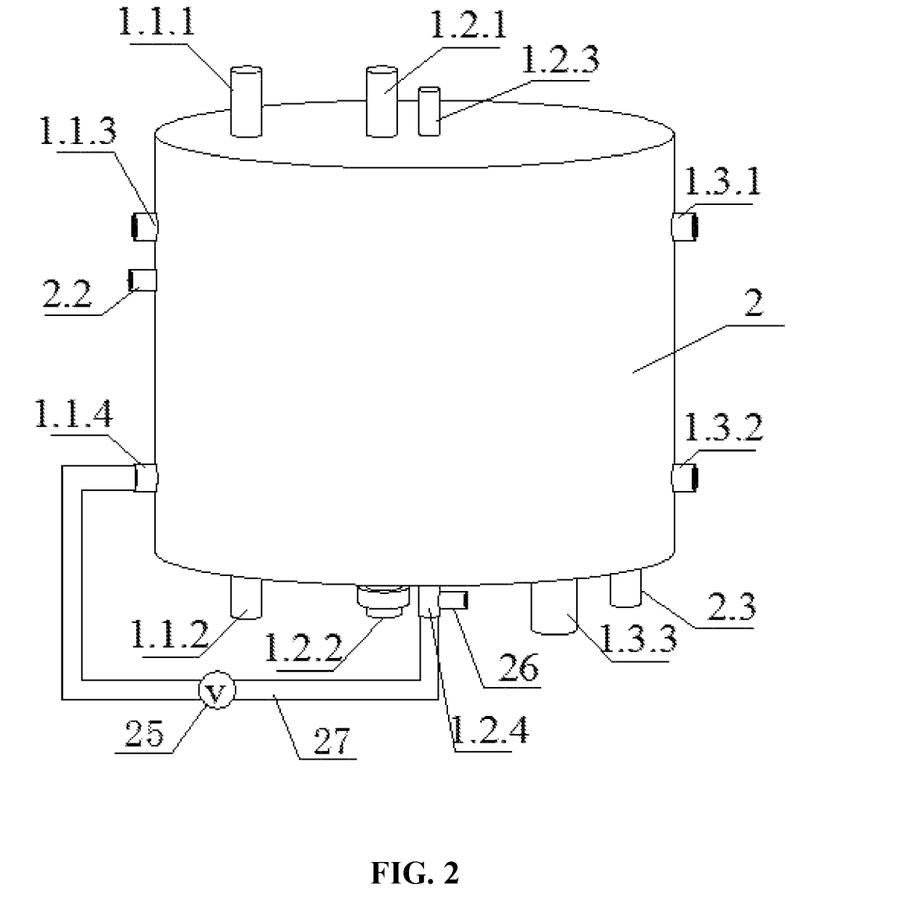
FIG. 2 is a schematic diagram of a bioreactor module in FIG. 1.
Figure 3:
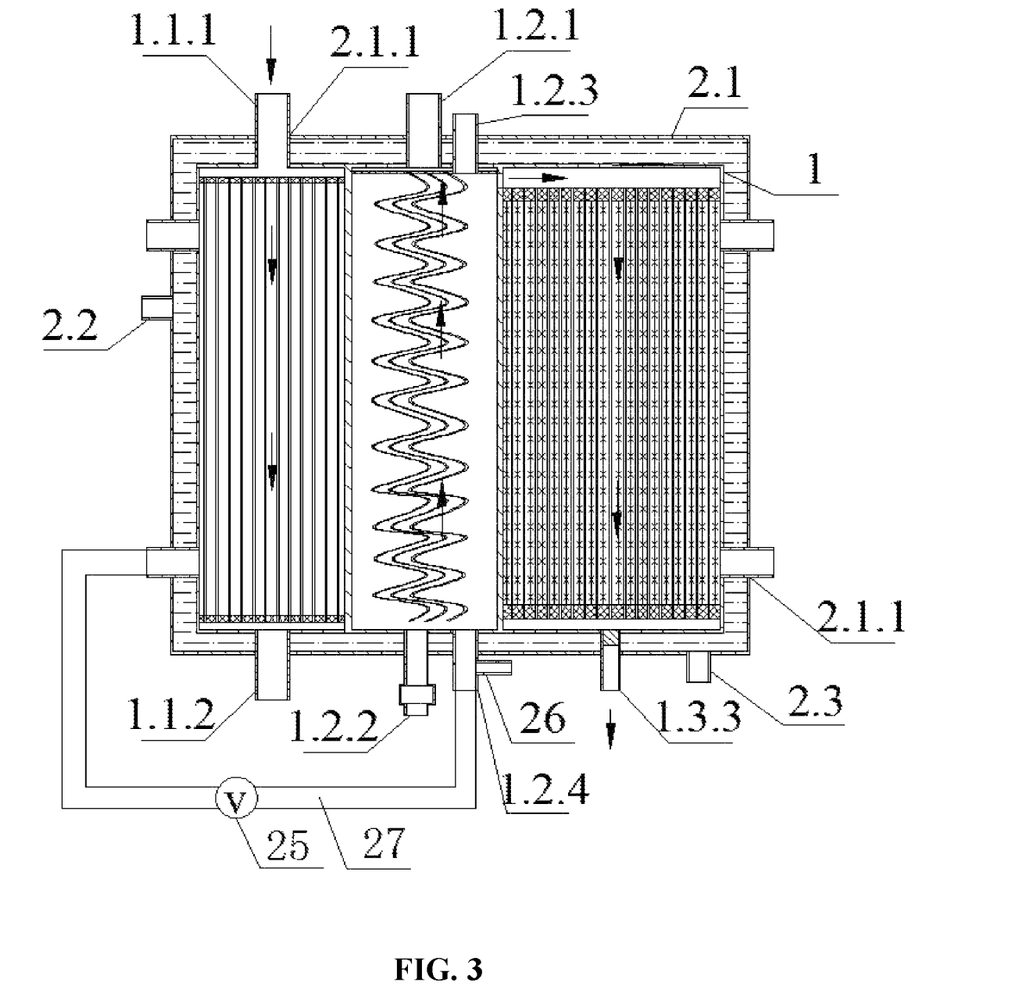
FIG. 3 is a cross-sectional view of FIG. 2.

The upper end of the container 1.4 at the middle portion where the oxygenator 1.2 is located is further provided with a backup sample inlet 1.2.3 of the oxygenator that is in communication with the space under the sealed stent plate 21. The lower end of the container 1.4 at the middle portion where the oxygenator 1.2 is located is provided with an infusion sample inlet 1.2.2 for adding drugs to be infused.

The breathable fiber membrane tubes 9 is arranged in a zigzag manner and may be of a helical, serpentine, or other curved shape with its upper end in communication with the oxygen/carbon dioxide inlet 1.2.1 and closed at its lower end.

The plasma/pre-filled liquid outlet 1.3.3 is provided with a polyethersulfone filtration membrane 16, a polyethylene filtration membrane 16, or a polyethylene-vinyl alcohol filtration membrane having a membrane thickness of 100 µm±25 µm and a membrane pore size of 0.5 µm±0.1 µm.

In use, the oxygen/carbon dioxide inlet 1.2.1 is first opened and then the blood/pre-filled liquid inlet 1.1.1 and the plasma/pre-filled liquid outlet 1.3.3 are opened and saline is injected through the blood/pre-filled liquid 1.1.1 for pre-rinsing the bioreactor 1. Then the blood/pre-filled liquid 1.1.1 is closed and a suspension of microcarriers with liver cells is injected through the nutrient liquid/liver cell suspension inlet 1.3.1 into the reaction 1.3 under sterile conditions to fill the entire reactor 1.3 with the microcarrier cell suspension. Thereafter, blood of a pig model with acute liver failure is introduced into the plasma separator 1.1 through the blood/pre-filled liquid inlet 1.1.1. Once the blood has passed through the hollow fiber bundles 8, the blood cells and part of the plasma are discharged through the blood cell outlet 1.1.2 and the remaining plasma pass through the external connection pipe 27 into the inner container of the oxygenator 1.2 under the action of the separation pump 25, enter the inner container of the reactor 1.3 through the communication hole 12, and are finally discharged from the reactor 1.3 through the plasma/pre-filled outlet 1.3.3. The blood cells and the part of plasma discharged through the blood cell outlet 1.1.2 are mixed with the plasma discharged through the plasma/pre-filled liquid outlet 1.3.3 to be reinfused into the pig body, thereby completing a therapeutic cycle loop. During the therapy, gas is charged through the oxygen/carbon dioxide inlet 1.2.1 into the inner container of the oxygenator 1.2 and enters the breathable fiber membrane tubes 9 from the upper end thereof. Since the breathable fiber membrane tubes 9 are placed in the inner container of the oxygenator 1.2, the cycle therapy of plasma can be maintained for up to several dozen hours with a certain dissolved oxygen and pH (adjusted through carbon dioxide). After the therapy, Kaplan-Meier survival analysis showed that such a therapy can significantly prolong the survival time of the animal subject.

At the beginning of the therapy, blood of a patient with liver failure is removed from the body, and then enters the integrated on-line monitoring and thermostatic heating apparatus for bioartificial liver through the blood/pre-filled liquid inlet 1.1.1. The blood enters the bioreactor 1 for detoxification and the detoxified blood is re-infused into the body of the patient or the animal subject through the blood reinfusion port 7.

During the therapy, the biochemical monitoring device 13 uses the upstream biochemical index probe 13.3 and the downstream biochemical index probe 13.4 at its two ends respectively to monitor variations of indexes such as bilirubin, ammonia, creatinine, urea nitrogen, liver enzymes, albumin, hemoglobin, red blood cells, white blood cells in the plasma in and out of the bioreactor 1. The monitoring and controlling apparatus 13.1 acquires and processes the monitored data in real time and feeds back to the entire apparatus through the signal feedback apparatus 13.2 to carry out control.

After the therapy, used consumables are disposed of. The polyethersulfone filtration membrane 16, the blood pipeline, and the like are removed from the artificial liver support device and disposed of in accordance with the disposal procedures of the hospital facilities.

Unless otherwise indicated, the numerical ranges involved in the invention include the end values. While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. An apparatus for a bioartificial liver device, the apparatus comprising the following elements connected to one another in sequence:
    a blood inlet;
    a blood pump;
    an arterial drip chamber;
    a bioreactor module, the bioreactor module comprising a thermostatic water tank and a bioreactor disposed in the thermostatic water tank;
    a venous drip chamber; and
    a blood reinfusion port;
wherein
    the bioreactor comprises a container, and a first partition and a second partition which are disposed in the container; the first partition and the second partition separate the container to form a plasma separator, an oxygenator, and a reactor;
    the plasma separator and the oxygenator are connected through an external connection pipe; the external connection pipe is equipped with a separation pump; the second partition comprises a communication hole, and the reactor and the oxygenator are connected through the communication hole;
    the container comprises a blood/pre-filled liquid inlet at an upper end thereof and a blood cell outlet at a lower end thereof; the plasma separator comprises hollow fiber bundles; the blood/pre-filled liquid inlet communicates with the blood cell outlet through the hollow fiber bundles in the plasma separator;
    the container also comprises an oxygen/carbon dioxide inlet at the upper end thereof, the oxygenator comprises breathable fiber membrane tubes, and the oxygen/carbon dioxide inlet communicates with the breathable fiber membrane tubes in the oxygenator;
    the container further comprises a nutrient liquid/liver cell suspension inlet, a nutrient liquid/liver cell suspension outlet, and a plasma/pre-filled liquid outlet; the reactor comprises a plurality of hollow fiber membrane tubes and a plurality of wool yarns; the communication hole communicates with the plasma/pre-filled liquid outlet through the plurality of hollow fiber membrane tubes; the plurality of wool yarns is parallel to, spaced from, and alternates with the plurality of the hollow fiber membrane tubes;
    the thermostatic water tank comprises a shell, and a hot water inlet and a hot water outlet disposed on the shell; the shell encloses the bioreactor; the shell comprises a plurality of bores corresponding to inlets and outlets of the bioreactor; the inlets and outlets of the bioreactor are filled with nozzles comprising an outer wall, and the outer wall of the nozzles is in sealed connection with walls enclosing the bores; and
    the blood/pre-filled liquid inlet is connected to an outlet of the arterial drip chamber, and the plasma/pre-filled liquid outlet and the blood cell outlet are both connected to an inlet of the venous drip chamber.

2. The apparatus of claim 1, wherein the external connection pipe comprises a liquid inlet end connected to a lower end of the plasma separator, and a liquid outlet end connected to a lower end of the oxygenator; and the communication hole is located at an upper end of the second partition.

3. The apparatus of claim 2, wherein the oxygenator further comprises a horizontally disposed sealed stent plate; the sealed stent plate is located above the communication hole and comprises a plurality of orifices; an upper end of the breathable fiber membrane tubes is clamped in the orifices; a space exists between the sealed stent plate and a top wall of the oxygenator, and the breathable fiber membrane tubes communicate with the oxygen/carbon dioxide inlet through the space formed by the sealed stent plate and the top wall of the oxygenator.

4. The apparatus of claim 2, wherein two polyurethane resin stent plates are horizontally disposed at an upper end and a lower end of the plasma separator, respectively; the two polyurethane resin stent plates are spaced from a top end and a bottom end of the plasma separator; the two polyurethane resin stent plates comprise a plurality of through holes, two ends of the hollow fiber bundle are clamped in the through holes of the two polyurethane resin stent plates, respectively; and the liquid inlet end of the external connection pipe is located between the two polyurethane resin stent plates.

5. The apparatus of claim 3, wherein two polyurethane resin stent plates are horizontally disposed at an upper end and a lower end of the plasma separator, respectively; the two polyurethane resin stent plates are spaced from a top end and a bottom end of the plasma separator; the two polyurethane resin stent plates comprise a plurality of through holes, two ends of the hollow fiber bundle are clamped in the through holes of the two polyurethane resin stent plates, respectively; and the liquid inlet end of the external connection pipe is located between the two polyurethane resin stent plates.

6. The apparatus of claim 2, wherein two polyurethane resin stent plates are horizontally disposed at an upper end and a lower end of the reactor, respectively; the two polyurethane resin stent plates are spaced from a top end and a bottom end of the reactor; the two polyurethane resin stent plates comprise a plurality of through holes, two ends of the hollow fiber membrane tubes are clamped in the through holes of the two polyurethane resin stent plates, respectively; the communication hole is located above the polyurethane resin stent sheets; the nutrient liquid/liver cell suspension inlet and outlet are located between the two polyurethane resin stent sheets.

7. The apparatus of claim 3, wherein two polyurethane resin stent plates are horizontally disposed at an upper end and a lower end of the reactor, respectively; the two polyurethane resin stent plates are spaced from a top end and a bottom end of the reactor; the two polyurethane resin stent plates comprise a plurality of through holes, two ends of the hollow fiber membrane tubes are clamped in the through holes of the two polyurethane resin stent plates, respectively; the communication hole is located above the polyurethane resin stent sheets; and the nutrient liquid/liver cell suspension inlet and outlet are located between the two polyurethane resin stent sheets.

8. The apparatus of claim 1, wherein two polyurethane resin stent plates are horizontally disposed at an upper end and a lower end of the plasma separator, respectively; the plasma separator further comprises an auxiliary inlet and an auxiliary outlet disposed between the two polyurethane resin stent plates; the oxygenator comprises an auxiliary outlet at a lower end thereof; the liquid inlet end of the external connection pipe communicates with the auxiliary outlet of the plasma separator; the liquid outlet end of the external connection pipe communicates with the auxiliary outlet of the oxygenator.

9. The apparatus of claim 1, wherein the wool yarns comprise a plurality of uniformly distributed wools woven from velvets.

10. The apparatus of claim 1, further comprising a biochemical monitoring device; wherein the biochemical monitoring device comprises a monitoring and controlling apparatus, a signal feedback apparatus, and an upstream biochemical index probe and a downstream biochemical index probe connected to the monitoring and controlling apparatus through electrical signals; the upstream biochemical index probe is disposed close to the blood inlet, and the downstream biochemical index probe is disposed close to the blood reinfusion port.

11. The apparatus of claim 1, wherein branch pipes for adding drug or liquid are provided on the arterial drip chamber, on the venous drip chamber, and between the blood pump and the blood inlet, respectively; a heparin branch pipe for injecting heparin is provided between the blood pump and the arterial drip chamber; an air monitoring device is provided between the venous drip chamber and the blood reinfusion port; a heating apparatus for heating water entering the thermostatic water tank and a temperature regulation apparatus for regulating a water temperature are provided between the arterial drip chamber and the bioreactor module.

12. The apparatus of claim 1, further comprising a plurality of pressure detection devices disposed on the arterial drip chamber, on the venous drip chamber, and between the blood inlet and the blood pump, respectively.

* * * * *